United States Patent [19]

Iijima et al.

[11] Patent Number: 4,663,319
[45] Date of Patent: May 5, 1987

[54] 3-(1,3-DITHIOL-2-YLIDENE)-2,4-DIOXOPYR-ROLIDINES, -PIPERIDINES, AND -HEXAHYDROAZEPINES AND USE THEREOF AGAINST HEPATIC DISEASES

[75] Inventors: Ikuo Iijima, Urawa; Koichi Homma, Tokyo; Yutaka Saiga, Ageo; Yuzo Matsuoka, Tondabayashi; Mamoru Matsumoto, Nara, all of Japan

[73] Assignee: Tanabe Seiysku Co., Ltd., Osaka, Japan

[21] Appl. No.: 689,261

[22] Filed: Jan. 7, 1985

[30] Foreign Application Priority Data

Jan. 14, 1984 [GB] United Kingdom ............... 8401010
Apr. 11, 1984 [GB] United Kingdom ............... 8409431

[51] Int. Cl.$^4$ ................... A61K 31/55; A61K 31/445; C07D 409/04; C07D 409/14
[52] U.S. Cl. ..................................... 514/212; 514/315; 514/318; 514/326; 514/328; 514/340; 514/422; 514/423; 514/425; 540/524; 540/526; 546/193; 546/207; 546/208; 546/219; 546/220; 546/243; 546/275; 548/524; 548/527; 548/534; 548/544
[58] Field of Search ...... 260/239 B, 239 BE, 239 BF, 260/193; 546/207, 208, 219, 220, 243, 275; 548/524, 527, 544, 534; 514/212, 336, 315, 318, 326, 328, 422, 423, 425, 340; 540/524, 526

[56] References Cited

U.S. PATENT DOCUMENTS 3,945,984 3/1976 Bukac et al. .................. 546/243

FOREIGN PATENT DOCUMENTS 11894 4/1970 Japan ............................. 548/544
65768 6/1976 Japan ............................. 546/243

Primary Examiner—Richard A. Schwartz
Assistant Examiner—Kurt G. Briscoe
Attorney, Agent, or Firm—Birch, Stewart, Kolasch and Birch

[57] ABSTRACT

Novel thioketene derivatives of the formula:

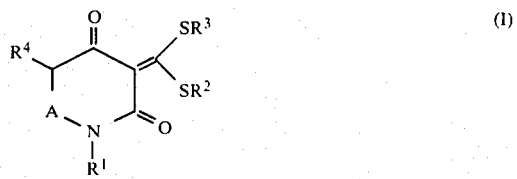

wherein $R^1$ is hydrogen atom, an alkyl group, a lower alkenyl group, a phenyl group or a group of the formula: —B—Y;

Y is a nitrogen-containing monocyclic heterocyclic group or a substituted or unsubstituted phenyl group;

B is a straight or branched lower alkylene group;

$R^2$ and $R^3$ are both a lower alkyl group or are combined together to form a group of the formula: —$CH_2CH_2$— or —CH=CH—;

$R^4$ is hydrogen atom, a lower alkyl group or a (lower alkoxy)carbonyl group;

A is a group of the formula: —$(CH_2)_n$— or —CH($COOR^5$)—;

n is an integer of 0, 1 or 2 and $R^5$ is a lower alkyl group, are disclosed. The compound (I) is useful as an agent for treating and protecting various liver diseases.

20 Claims, No Drawings

3-(1,3-DITHIOL-2-YLIDENE)-2,4-DIOXOPYRROLIDINES, -PIPERIDINES, AND -HEXAHYDROAZEPINES AND USE THEREOF AGAINST HEPATIC DISEASES

The present invention relates to novel thioketene derivatives and processes for the preparation thereof. More particularly, it relates to a thioketene derivative of the formula:

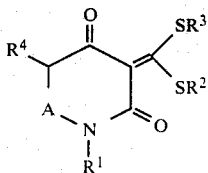

wherein
$R^1$ is hydrogen atom, an alkyl group, a lower alkenyl group, a phenyl group or a group of the formula: —B—Y;
Y is a nitrogen-containing monocyclic heterocyclic group or a substituted or unsubstituted phenyl group;
B is a straight or branched lower alkylene group;
$R^2$ and $R^3$ are both a lower alkyl group or combine together to form a group of the formula: —CH$_2$CH$_2$— or —CH=CH—;
$R^4$ is hydrogen atom, a lower alkyl group or a (lower alkoxy)carbonyl group;
A is a group of the formula: —(CH$_2$)$_n$— or —CH(COOR$^5$)—;
n is an integer of 0, 1 or 2; and
$R^5$ is a lower alkyl group; and processes of the preparation thereof.

It also relates to a carbamoyl acetate derivative of the formula:

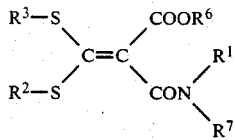

wherein $R^6$ is a lower alkyl group, $R^7$ is hydrogen atom or a group of the formula: —A'—CH$_2$COOR$^8$, A' is a group of the formula: —CH$_2$— or —CH(COOR$^5$)—, $R^8$ is a lower alkyl group and $R^1$, $R^2$, $R^3$ and $R^5$ are the same as defined above.

This invention includes pharmaceutically acceptable salts of the compounds (I) and (II) wherein $R^1$ is a group of the formula: —B—Y and Y is a nitrogen-containing monocyclic heterocyclic group or an amino-phenyl group.

The liver is an organ having various functions such as detoxication, carbohydrate metabolism, lipid metabolism, protein metabolism, production and secretion of bile, production of blood coagulation factors, control of hormones, regeneration of liver cells, storage of living body-constituting elements (e.g. fats, glycogen, proteins, vitamins), and the like. These functions are acutely or chronically disordered by various causes such as virus, drugs, poisons, alcohols, insufficient nutrition, vascular dysfunction of the liver, obstruction of the bile duct, or the like. These liver function disorders appear clinically in the form of a viral hepatitis, drug-induced hepatopathy, alcoholic hepatitis, congestive hepatitis, hepatic disease caused by bile-congestion, fatty liver, jaundice, and hepatocirrhosis, or the like.

The thioketene derivatives (I) are novel compounds and are useful as therapeutic or prophylactic agents for hepatic diseases because they show excellent activities for alleviating or curing hepatic damage and also for protecting the liver from hepatic damage.

The thioketene derivatives (I) of the present invention include compounds of the formula (I) wherein $R^1$ is hydrogen atom, an alkyl group (e.g. methyl, ethyl, propyl, butyl, pentyl, hexyl, heptyl, octyl, nonyl, or decyl), a lower alkenyl (e.g. vinyl, allyl or butenyl), phenyl, or a group of the formula: —B—Y wherein Y is a nitrogen-containing monocyclic heterocyclic group (e.g. pyridyl, pyrrolyl), or a phenyl group unsubstituted or substituted by one or two substituents selected from a halogen atom (e.g. fluorine, chlorine, bromine or iodine), a lower alkyl (e.g. methyl, ethyl, propyl, or butyl), a lower alkoxy group (e.g. methoxy, ethoxy, propoxy, or butoxy), nitro, amino, or benzyloxycarbonylamino, B is a straight or branched lower alkylene group (e.g. methylene, ethylene, trimethylene or propylene); $R^2$ and $R^3$ are both a lower alkyl (e.g. methyl, ethyl, propyl or butyl) or combine together to form a group of the formula: —CH$_2$CH$_2$— or —CH=CH—; $R^4$ is hydrogen atom, a lower alkyl group (e.g. methyl, ethyl, propyl or butyl) or a (lower alkoxy)carbonyl group (e.g. methoxycarbonyl, ethoxycarbonyl, propoxycarbonyl or butoxycarbonyl); A is a group of the formula: —(CH$_2$)$_n$— or —CH(COOR$^5$)—; n is an integer of 0, 1 or 2 and $R^5$ is a lower alkyl group (e.g. methyl, ethyl, propyl or butyl).

Preferred compounds are compounds of the formula (I) wherein $R^1$ is hydrogen atom, an alkyl group, a lower alkenyl group, a phenyl group or a group of the formula: —B—Y; Y is a nitrogen-containing monocyclic heterocyclic group or a substituted or unsubstituted phenyl group; B is a straight or branched lower alkylene group; $R^2$ and $R^3$ are both lower alkyl groups or combine together to form a group of the formula: —CH$_2$CH$_2$— or —CH=CH—; $R^4$ is hydrogen atom, a lower alkyl group or a (lower alkoxy)carbonyl group; A is a group of the formula: —(CH$_2$)$_n$— or —CH(COOR$^5$)—; n is an integer of 1; and $R^5$ is a lower alkyl group.

Other preferred compounds are compounds of the formula (I) wherein $R^1$ is an alkyl group, a lower alkenyl group, a phenyl group or a group of the formula: —B—Y; Y is a phenyl group or a phenyl group having a substituent selected from a group consisting of a halogen atom or a lower alkoxy; B is a straight lower alkylene group; $R^2$ and $R^3$ combine together to form a group of the formula: —CH$_2$CH$_2$— or —CH=CH—; $R^4$ is hydrogen atom, a lower alkyl group or a (lower alkoxy)carbonyl group; A is a group of the formula: —(CH$_2$)$_n$— or —CH(COOR$^5$)—; n is an integer of 1; and $R^5$ is a lower alkyl group.

Still another preferred compounds are those of the formula (I) wherein $R^1$ is hydrogen atom, methyl, ethyl, n-butyl, n-hexyl, n-octyl, n-decyl, allyl, phenyl, 3-pyridylmethyl, benzyl, phenethyl, 4-chlorobenzyl, 3,4-dichlorobenzyl, 4-methylbenzyl, 4-methoxylbenzyl, 3,4-dimethoxybenzyl, 4-nitrobenzyl, 4-aminobenzyl or 4-(N-benzyloxycarbonyl-amino)benzyl; and $R^2$ and $R^3$ are both methyl or combine together to form a group of the formula: —CH$_2$CH$_2$— or —CH=CH—; and $R^4$ is hydrogen atom, methyl, ethyl, or ethoxycarbonyl; A is a group of the formula: —(CH$_2$)$_n$— or —CH(COOR$^5$)—; n is an integer of 0, 1 or 2; and R$^5$ is ethyl.

Other preferred compounds are compounds of the formula (I) wherein R$^1$ is methyl, ethyl, n-butyl, n-hexyl, allyl, phenyl, 3-pyridylmethyl, benzyl, phenethyl, 4-chlorobenzyl, 4-methylbenzyl, 4-methoxybenzyl, or 3,4-dimethoxybenzyl; R$^2$ and R$^3$ combine together to form a group of the formula: —CH$_2$CH$_2$— or —CH=CH—; R$^4$ is hydrogen atom, methyl, ethyl or ethoxycarbonyl; A is a group of the formula: —(CH$_2$)$_n$— or —CH(COOR$^5$)—; n is an integer of 1; and R$^5$ is ethyl.

Still other preferred compounds are compounds of the formula (I) wherein R$^1$ is methyl, ethyl, benzyl, 4-chlorobenzyl or 4-methoxybenzyl; R$^2$ and R$^3$ combine together to form a group of the formula: —CH$_2$CH$_2$— or —CH=CH—; R$^4$ is hydrogen aotm, methyl, ethyl or ethoxycarbonyl; A is a group of the formula: —(CH$_2$)$_n$— or —CH(COOR$^5$)—; n is an integer of 1; and R$^5$ is ethyl.

The compounds of the formula (I) and (II) wherein R$^1$ is a group of the formula: —B—Y and Y is a nitrogen-containing monocyclic heterocyclic group or an amino-phenyl group may be used in the form of either a free base or a pharmaceutically acceptable salt thereof. Suitable examples of the salt include inorganic acid addition salts such as hydrochloride, hydrobromide or sulfate, and organic acid addition salts such as aromatic sulfonates (e.g., benzenesulfonate, toluenesulfonate) or alkylsulfonates (e.g., methanesulfonate, ethanesulfonate). These salts may be prepared by reacting said compound (I) or (II) with a stoichiometrically equimolar amount of an inorganic or organic acid.

The compounds of the formula (I) and wherein R$^4$ is a lower alkyl group of a (lower alkoxy)carbonyl group; or A is a group of the formula: —CH(COOR$^5$)— include two optical isomers due to the asymmetric carbon atom involved. Besides, the compounds of the formula (I) wherein R$^4$ is a lower alkyl group or a (lower alkoxy)carbonyl group and A is a group of the formula: —CH(COOR$^5$)— include two stereoisomers (i.e. cis- and trans-isomers), and each of said stereoisomers further includes two optical isomers. The present invention includes within its scope either one of these isomers and a mixture thereof.

On the other hand, the carbamoyl acetate derivative (II) is useful as an intermediate in the synthesis of the thioketene derivative (I). However, since said carbamoyl acetate derivative (II) have a therapeutic effect for alleviating or curing hepatic damages, it may also be used as a therapeutic or prophylactic agent for hepatic diseases.

According to the present invention, the compounds (I) can be prepared by the following processes.

PROCESS A

The compound (I) carn be prepared by reacting a compound of the formula:

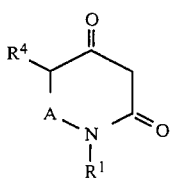

(III)

wherein R$^1$, R$^4$ and A are the same as defined above, with a compound of the formula:

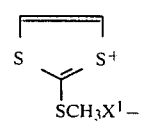

(IV)

wherein X$^1$ is a halogen atom, or by reacting the compound (III) with carbon disulfide and a compound selected from a lower alkyl halide, a 1,2-dihalogenoethane and a 1,2-dihalogenoethylene.

PROCESS B

A compound of the formula:

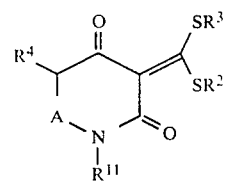

(I-a)

wherein R$^{11}$ is an alkyl group, a lower alkenyl group, a phenyl group or a group of the formula: —B—Y and Y, B, R$^2$, R$^3$, R$^4$ and A are the same as defined above, can be prepared by reacting a compound of the formula:

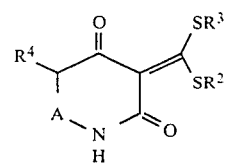

(I-b)

wherein R$^2$, R$^3$, R$^4$ and A are the same as defined above, with a compound of the formula:

R$^{11}$—X$^2$ (V)

wherein X$^2$ is a halogen atom and R$^{11}$ is the same as defined above.

PROCESS C

A compound of the formula:

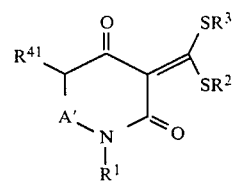

(I-c)

wherein R$^{41}$ is hydrogen atom or a (lower alkoxy)carbonyl and R$^1$, R$^2$, R$^3$ and A' are the same as defined above, can be prepared by the step or steps of
(a) reacting a compound of the formula:

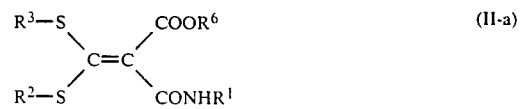

(II-a)

wherein $R^1$, $R^2$, $R^3$ and $R^6$ are the same as defined above, with a compound of the formula:

$$R^9-CH=CH-COOR^8 \qquad (VI)$$

wherein $R^9$ is hydrogen atom or a group of the formula: $-COOR^5$, $R^8$ and $R^5$ are the same defined above, to give a compound of the formula:

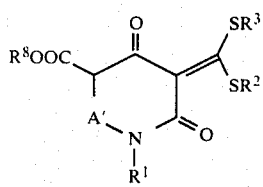
(I-d)

wherein $R^1$, $R^2$, $R^3$, $R^8$ and A' are the same as defined above, or (b) subjecting a compound of the formula:

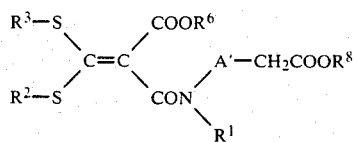
(II-b)

wherein $R^1$, $R^2$, $R^3$, $R^6$, $R^8$ and A' are the same as defined above, to intramolecular cyclization to give the compound (I-d), and (c) if required, further treating said compound (I-d) with an alkali or an acid to give a compound of the formula:

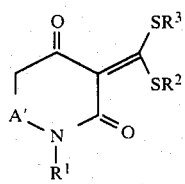
(I-e)

wherein $R^1$, $R^2$, $R^3$ and A' are the same as defined above.

PROCESS D

A compound of the formula:

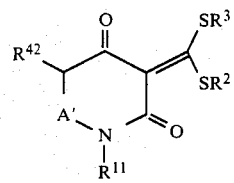
(I-f)

wherein $R^{42}$ is a lower alkyl group and $R^{11}$, $R^2$, $R^3$ and A' are the same as defined above, can be prepared by the steps of:

reacting a compound of the formula:

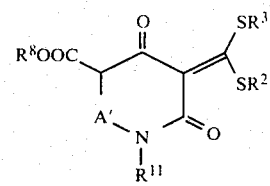
(I-d')

wherein $R^{11}$, $R^2$, $R^3$, $R^8$ and A' are the same as defined above with a lower alkyl halide to give a compound of the formula:

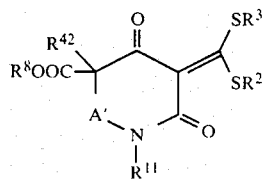
(I-f')

wherein $R^{11}$, $R^2$, $R^3$, $R^{42}$, $R^8$ and A' are the same as defined above, and then removing a group of the formula: $-COOR^8$ (wherein $R^8$ is the same as defined above).

PROCESS E

A compound of the formula:

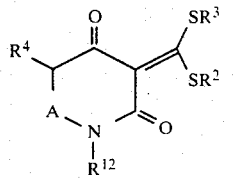
(I-g)

wherein $R^{12}$ is a group of the formula: $-B-Y$, Y is an aminophenyl and $R^2$, $R^3$, $R^4$ and A are the same as defined above, can be prepared by reducing a compound of the formula:

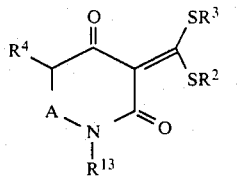
(I-h)

wherein $R^{13}$ is a group of the formula: $-B-Y$, Y is a nitrophenyl and $R^2$, $R^3$, $R^4$ and A are the same as defined above, or by removing an acyl group from a compound of the formula:

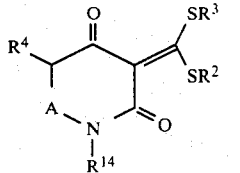
(I-i)

wherein $R^{14}$ is a group of the formula: —B—Y, Y is an acylamino-phenyl and $R^2$, $R^3$, $R^4$ and A are the same as defined above.

The processes are explained in more detail below.

PROCESSES A AND B

The reaction of the compound (III) with the compound (IV) or with carbon disulfide and a compound selected from a lower alkyl halide, a 1,2-dihalogenoethane and a 1,2-dihalogenoethylene as well as the reaction of the compound (I-b) with the compound (V) are carried out in the presence of a base in a solvent. In the compounds (IV) and (V), $X^1$ and $X^2$ are preferably chlorine, bromine or iodine.

Examples of the lower alkyl halide include methyl bromide, ethyl bromide, methyl iodide, ethyl iodide, etc. The 1,2-dihalogenoethane includes 1,2-dichloroethane, 1,2-dibromoethane, etc. The 1,2-dihalogenoethylene includes 1,2-dichloroehtylene, 1,2-dibromoethylene, etc.

The base to be used in the above reactions includes inorganic bases and organic bases, but in the reaction of the compound (I-b) with the compound (V), an inorganic base is preferably used. Suitable examples of the inorganic base are alkali metal hydrides (e.g. sodium hydride, potassium hydride), alkali metal hydroxides (e.g. sodium hydroxide, potassium hydroxide), and alkali metal carbonates (e.g. sodium carbonate, potassium carbonate). Suitable examples of the organic base are alkali metal alkoxide (e.g. sodium methoxide, sodium ethoxide), 1,5-diazabicyclo[4.3.0]non-5-ene, 1,5-diazabicyclo[5.4.0]undec-5-ene.

Suitable examples of the solvent are ether, tetrahydrofuran, dioxane, N,N-dimethylformamide, N,N-dimethylacetamide, dimethylsulfoxide, dimethoxyethane, or the like. These reactions are preferably carried out at a temperature of 0 to 80° C.

PROCESS C

The reaction of the compound (II-a) with the compound (VI) can be carried out in the presence of a base in a solvent. The base to be used in the reaction includes inorganic and organic bases. Examples of the inorganic base include an alkali metal hydrive (e.g. sodium hydride or potassium hydride), an alkali metal hydroxide (e.g. sodium hydroxide or potassium hydroxide), and an alkali metal carbonate (e.g. sodium carbonate or potassium carbonate). Examples of the organic base include an alkali metal alkaoxide (e.g. sodium methoxide or sodium ethoxide), n-butyl lithium and lithium diisopropylamide. Dimethylformamide, dimethylsulfoxide, dimethoxyethane, tetrahydrofuran, ether or benzene are suitable as the solvent. It is preferred to carry out the reaction at a temperature of 0° to 80° C.

The intramolecular cyclization of the compound (II-b) can be carried out in the presence of a base in a solvent. The base to be used in the reaction includes organic bases such as alkali metal alkoxide (e.g. sodium methoxide, sodium ethoxide). Benzene, methanol, ethanol or tetrahydrofuran are suitable as the solvent. It is preferred to carry out the reaction at a temperature of 0° C.–80° C.

In the above-mentioned formulae (II-a), (II-b) and (VI), suitable examples of the group $R^5$, $R^6$ and $R^8$ include a lower alkyl or one to 4 carbon atoms such as methyl, ethyl, propyl or butyl.

The subsequent optional treatment of the compound (I-d) with the alkali or acid can be carried out in a solvent. Examples of the alkali include an alkali metal hydroxide (e.g. sodium hydroxide or potassium hydroxide), an alkali metal carbonate (e.g. sodium carbonate or potassium carbonate), an alkali metal bicarbonate (e.g. sodium bicarbonate or potassium bicarbonate), and ammonia. Examples of the acid include a mineral acid (e.g. hydrochloric acid or sulfuric acid). Water, methanol, ethanol, tetrahydrofuran, dioxane or a mixture thereof are suitable as the solvent. It is preferred to carry out the reaction at a temperature of 30° to 100° C.

PROCESS D

The reaction of the compount (I-d') with a lower alkyl halide can be carried out in the presence of a base in a solvent. Suitable examples of the lower alkyl halide include methyl bromide, ethyl bromide, methyl iodide, ethyl iodide. The base to be used in the reaction includes inorganic and organic bases. Suitable examples of the inorganic base include an alkali metal hydroxide (e.g. sodium hydroxide, potassium hydroxide), an alkali metal hydride (e.g. sodium hydride, potassium hydride) and an alkali metal carbonates (e.g. sodium carbonate, potassium carbonate). Suitable examples of the organic base include an alkali metal alkoxide (e.g. sodium methoxide, sodium ethoxide). Dimethylforamide, tetrahydrofuran, dioxane, dimethylacetamide, dimethylsulfoxide, dimethoxyethane, ether or the like are suitable as the solvent. It is preferred to carry out the reaction at a temperature of 0° to 80° C.

Removal of the group of the formula: —$COOR^8$ from the compound (I-f') can be accomplished by treating it with an alkali in a solvent followed by heating the resulting compound in a solvent. Suitable examples of the alkali include an alkali metal hydroxide (e.g. sodium hydroxide, potassium hydroxide). Examples of the solvent to be used in the alkali treatment include methanol, ethanol, tetrahydrofuran, dioxane, water or a mixture thereof. After the alkali treatment, said alkoxy carbonyl group (—$COOR^8$) may be readily removed by heating the compound in question at about 40°–100° C.

PROCESS E

The reduction of the compound (I-h) can be carried out in the presence of a catalyst in a solvent. Suitable examples of the catalyst include Pd/C, Pt, Raney nickel. Methanol, ethanol, ethyl acetate are suitable as the solvent. It is preferred to carry out the reaction at a temperature of 20° to 80° C.

On the other hand, the removal of an acyl group from the compound (I-i) can be carried out in a conventional manner. For example, the acyl group can be removed by treating said compound (I-i) with a mineral acid (e.g. hydrobromic acid, hydrochloric acid, sulfuric acid), or by catalitically reducing the compound (I-i) in the presence of a catalyst (e.g. Pd/C, Pt).

Among the starting compounds of the present invention, the compounds (II-a) and (II-b) are novel compounds and may be prepared, for example, according to either one of the methods (F) and (G) shown by the following reaction scheme:

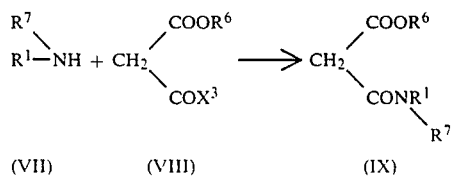

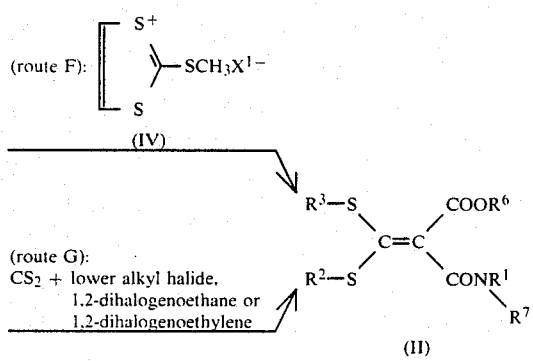

wherein $X^3$ is a halogen atom, and $R^1$, $R^2$, $R^3$, $R^6$, $R^7$ and $X^1$ are the same as defined above.

The compound (IX) may be prepared by reacting the compounds (VII) and (VIII) in a solvent (e.g., methylene chloride, benzene, ethyl acetate, chloroform, ether) in the presence of an acid acceptor (e.g., benzylamine, triethylamine, pyridine, sodium hydroxide, sodium bicarbonate) at 0° to 50° C. When an excess of the compound (VII) is used, it is not always necessary to use the acid acceptor because said compound (VII) serves as the acid acceptor. The compound of the formula (VIII) in which $X^3$ is chlorine atom is especially preferred for use as one of the starting compounds.

The compound (II) may be prepared by reacting the compounds (IX) and (IV) in a solvent (e.g., dimethylsulfoxide, dimethylformamide, 1,2-dimethoxyethane, tetrahydrofuran, benzene, ether) in the presence of a base (e.g., sodium hydride, potassium hydride, sodium hydroxide, potassium hydroxide, potassium carbonate, sodium carbonate, sodium methoxide) at 10° to 80° C. (route F). Preferred examples of the group $X^1$ in the compound (IV) are chlorine, bromine or iodine. Alternatively, the compound (II) may be prepared by reacting the compound (IX) with carbon disulfide and a compound selected from lower alkyl halide, 1,2-dihalogenoethane and 1,2-dihalogenoethylene (route G). This reaction may be carried out in a solvent (e.g., dimethylformamide, dimethylsulfoxide, dimethoxyethane, methanol, ethanol, benzene, water or a mixture thereof) in the presence of a base (e.g., sodium hydride, potassium hydride, sodium hydroxide, potassium hydroxide, potassium carbonate, sodium carbonate, sodium methoxide) at 0° to 80° C. The lower alkyl halide includes methyl bromide, ethyl bromide, methyl iodide, ethyl iodide, etc. The 1,2-dihalogenoethane includes 1,2-dichloroethane, 1,2-dibromoethane, etc. The 1,2-dihalogenoethylene includes 1,2-dichloroethylene, 1,2-dibromoethylene, etc. The 1,2-dihalogenoethylene exists in the form of either cis- or trans-isomers, among which the cis-isomer is especially preferred for use in the present invention.

The starting compound (VII), wherein $R^7$ is a group of the formula: $-A'-CH_2COOR^8$ and $A'$ and $R^8$ are the same as defined above, may be prepared by reacting a compound of the formula: $R^1NH_2$ (wherein $R^1$ is the same as defined above) with the compound (VI); or alternatively, by reacting a compound of the formula: $R^{15}CHO$ (wherein $R^{15}$ is hydrogen atom, an alkyl group, a lower alkenyl group, a substituted or unsubstituted phenyl group or a group of the formula: $-B-Y$ and B and Y are the same as defined above) with a compound of the formula: $H_2N-A'-CH_2COOR^8$ (wherein $A'$ and $R^8$ are the same as defined above) and then reducing the resulting product.

On the other hand, among the starting compounds (III) to be used in the process (A), the compounds (III) wherein A is a group of the formula: $-(CH_2)_n-$ and n is an integer of 0 or 1 may be prepared according to per se known methods as described in Collection Czeckoslov. Chem. Commun., 35, 3280 (1970), J. of Antibiotics, 33, 173 (1980), and Tetrahedron Letters, 369 (1979). Alternatively it may also be prepared by reacting an aminocarboxylic acid ester (X) and diketene as shown in the following reaction scheme H, or subjecting the compound (XII) to intramolecular cyclization as shown in the reaction scheme I:

Reaction Scheme H

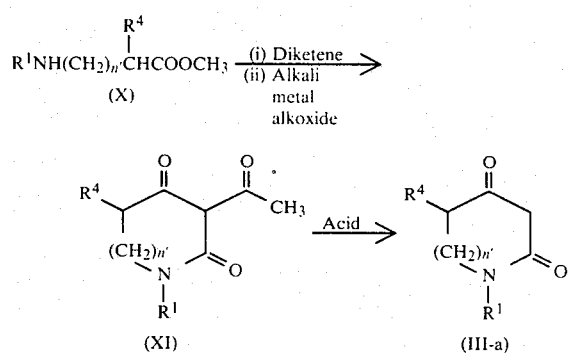

Reaction Scheme I

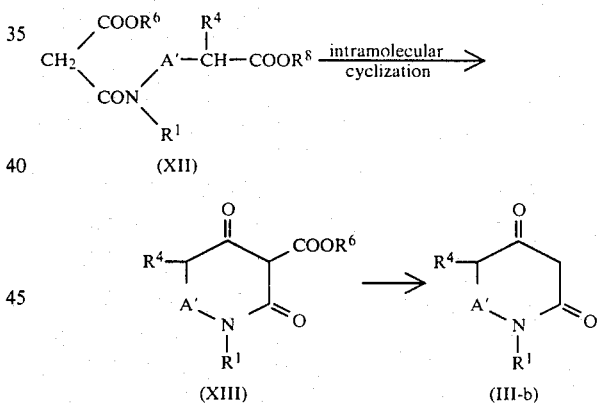

wherein n' is an integer of 0 or 1 and $R^1$, $R^4$, $R^6$, $R^8$ and $A'$ are the same as defined above.

In the above reaction scheme H, the compound (X) is reacted with diketene in a solvent (e.g., methanol, ethanol, benzene) at a temperature of 0° to 50° C. and then treated with alkali metal alkoxide (e.g., sodium methoxide, sodium ethoxide) at a temperature of 10° to 80° C. to give the compound (XI). The compound (XI) thus obtained is then reacted with an acid (e.g. hydrochloric acid, hydrobromic acid, acetic acid) in a solvent (e.g. ethanol, water, tetrahydrofuran) with heating. The compound (X) wherein n' is an integer of 1 is prepared by reacting an amine of the formula: $R^1-NH_2$ (wherein $R^1$ is as defined above) with methyl acrylate derivative.

The intramolecular cyclization of the compound (XII) may be carried out in the same manner as that of the compound (II-b), and the subsequent removal of a (lower alkoxy)carbonyl may be carried out by heating the compound (XIII) in a solvent (e.g. aqueous acetonitrile, aqueous tetrahydrofuran or water).

The compounds (III) wherein n is an interger of 1 or 2 may be prepared by reacting a compound (XII) with a compound (V) as shown in the following reaction scheme J:

Reaction Scheme J

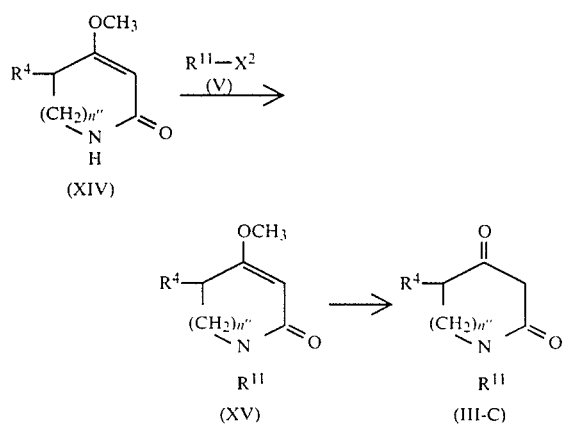

wherein n″ is an integer of 1 or 2, and $R^{11}$, $R^4$ and $X^2$ are as defined above.

In the above reaction scheme J, the reaction of the compound (XIV) with the compound (V) is carried out in the presence of a base (e.g. sodium hydroxide, potassium hydroxide, sodium hydride, potassium hydride, sodium methoxide, potassium carbonate) to give the compound (XV), and the compound (XV) thus obtained is treated with an acid (e.g. hydrochloric acid, hydrobromic acid, acetic acid) at a temperature of 30° to 80° C. The compound (XIV) wherein n″ is an integer of 2 can be prepared, for example, by subjecting 3-methoxy-2-cyclohexene-1-one oxime [cf. Chem. Pharm. Bull., 19, 523 (1971)] to Beckmann rearrangement in a usual manner.

There are known a variety of causal factors inducing toxic liver damage, hepatitis and fatty liver. The predominant changes observed in these diseases are necrosis of liver cells, mesenchymal reaction and accumulation of lipid. The feature of necrosis depends on the causal factor and it can be classified into centrilobular necrosis, periportal necrosis and discrete lobular necrosis. In experiments, the centrilobular necrosis is induced by carbon tetrachloride, and the degree of liver damage is determined by the measurement of liver weight and observation of liver color with the naked eye. The periportal necrosis and the discrete lobular necrosis associated with mesenchymal reaction are induced by allyl alcohol and D-galactosamine, respectively, and the degree of liver damage is determined by the measurement of activities of glutamic-pyruvic-transaminase (GPT) and glutamic-oxaloacetic-transaminase (GOT) in the blood plasma.

The compounds (I), (II) and their salts of the present invention have excellent activities for curing, preventing and alleviating various liver diseases, particularly liver diseases associated with centrilobular necrosis, liver diseases associated with periportal necrosis, liver diseases associated with discrete lobular necrosis and mesenchymal reaction, fatty liver, drug-induced hepatopathy, and congestive hepatitis. Accordingly, the compounds of the present invention are useful as a therapeutic or prophylactic agent for hepatic diseases in animals including humans, and are used, for example, for treating or preventing various diseases such as viral hepatitis, drug-induced hepatopathy, alcoholic hepatitis, fatty liver, jaundice, and also, the final symptom, i.e. hepatocirrhosis. Moreover, the compounds of the present invention also show stimulation of the liver function with low toxicity and hence with high safety. For example, when 1-benzyl-3-(1,3-dithiol-2-ylidene)-2,4-dioxopiperidine, one of the compounds of the present invention, was orally administered to mice in a dose of 1500 mg/kg, no mouse died during 7 days-observation after administration.

When the compounds (I), (II) and their salts of the present invention are used as a medicine, they can be administered in oral route or parenteral route (e.g. subcutaneous, intramuscular or intravenous route). The dose of the compounds (I), (II) and their salts may vary according to ages, sex, weights and states of patients, administration routes, severity of diseases, or the like, but is usually in the range of about 0.01 to 250 mg/kg/day, preferably 0.1 to 50 mg/kg/day.

The compounds (I), (II) and their salts can be used in conventional pharmaceutical preparations in admixture with conventional pharmaceutical carriers or diluents which are usually used for oral or parenteral preparations. The carriers include, for example, gelatine, lactose, glucose, sodium chloride, starches, magnesium stearate, talc, vegetable oils, and the like. The pharmaceutical preparations may be solid preparations such as tablets, sugar coating tablets, capsules, pills, or powders, or liquid preparations such as solutions, suspensions, or emulsions. These preparations may be sterilized. Moreover, various auxiliaries, stabilizers, wetting agents, emulsifiers, and other additives may optionally be added to the preparations.

The present invention is illustrated by the following Experiments and Examples, but it should not be construed to be limited thereto.

Throughout the specification and claims, the term "alkyl" denotes an alkyl having 1 to 10 carbon atoms, "lower alkenyl" denotes an alkenyl having 2 to 4 carbon atoms, "lower alkylene", "lower alkyl" and "lower alkoxy" denote an alkylene having 1 to 4 carbon atoms, an alkyl having 1 to 4 carbon atoms and an alkoxy having 1 to 4 carbon atoms, respectively. Besides, the term "1,3-dithiol" denotes "4,5-didehydro-1,3-dithiacyclopentane".

EXPERIMENT 1

Protection against acute hepatic damage induced by carbon tetrachloride:

Method: The test compounds were suspended in a 0.5% carboxylmethyl cellulose solution, and the suspension (test compound: 100 mg/10 ml/kg) was orally administered to ddY male mice (age: 5–6 weeks old, weight: 25–30 g, one group: 3 mice), and the animals were fasted. After 3 hours, a solution of carbon tetrachloride in olive oil was orally administered in a dose of 50 μl/5 ml olive oil/kg. After 3 hours, the test compound was again orally administered in the same dose as above. Weight of the animals was measured 24 hours after CCl₄ administration, and then, the animals were killed. Immediately, the liver was taken out, weighed and macroscopically observed. As the normal control, the 0.5% carboxymethyl cellulose solution and olive oil were orally administered to the animals instead of the suspension of test compound and the CCl₄ solution.

Besides, the CCl₄-control group was given the CCl₄ solution and the 0.5% carboxymethyl cellulose solution.

The therapeutic effect of the test compounds on liver damages was evaluated based on the suppressive % of the increase of relative liver weight calculated by the following equation and also based on the macroscopic observation of the liver as shown in Table 1. The term "relative liver weight" means weight (g) of the liver/100 g body weight.

Suppressive % of the increase of relative liver weight $$= \left[1 - \frac{\begin{array}{c}\text{Mean of relative}\\ \text{liver weight in}\\ \text{test compound}\\ \text{group}\end{array} - \begin{array}{c}\text{Mean of relative}\\ \text{liver weight in}\\ \text{normal control}\\ \text{group}\end{array}}{\begin{array}{c}\text{Mean of relative}\\ \text{liver weight in}\\ \text{CCl}_4\text{-control}\\ \text{group}\end{array} - \begin{array}{c}\text{Mean of relative}\\ \text{liver weight in}\\ \text{normal control}\\ \text{group}\end{array}}\right] \times 100$$

TABLE 1

| Macroscopic observation of the liver | (Criteria) Suppressive % of increasing of relative liver weight | | |
|---|---|---|---|
| | ≧20% | ≧−20% to <20% | <−20% |
| Almost the same as normal control group | AA | C | D |
| Showed a sign of amelioration from CCl₄— control group | A | C | D |
| Showed the same color or appearance as in CCl₄— control group | B | D | D |

Remarks:
AA means "significantly effective",
A, B and C mean "effective", and
D means "not effective"

The results of the above experiment are shown in the following Table 2.

TABLE 2

| Test compound Nos. and chemical names | Evaluation (Dose: 100 mg/kg × 2) |
|---|---|
| 1. 1-Methyl-3-(1,3-dithiol-2-ylidene)-2,4-dioxopiperidine | AA |
| 2. 1-Ethyl-3-(1,3-dithiol-2-ylidene)-2,4-dioxopiperidine | AA |
| 3. 1-n-Butyl-3-(1,3-dithiol-2-ylidene)-2,4-dioxopiperidine | AA |
| 4. 1-n-Hexyl-3-(1,3-dithiol-2-ylidene)-2,4-dioxopiperidine | AA |
| 5. 1-Allyl-3-(1,3-dithiol-2-ylidene)-2,4-dioxopiperidine | AA |
| 6. 1-Benzyl-3-(1,3-dithiol-2-ylidene)-2,4-dioxopiperidine | AA |
| 7. 1-(4-Chlorobenzyl)-3-(1,3-dithiol-2-ylidene)-2,4-dioxopiperidine | AA |
| 8. 1-(4-Methoxybenzyl)-3-(1,3-dithiol-2-ylidene)-2,4-dioxopiperidine | AA |
| 9. 1-(4-Methylbenzyl)-3-(1,3-dithiol-2-ylidene)-2,4-dioxopiperidine | AA |
| 10. 1-Phenethyl-3-(1,3-dithiol-2-ylidene)-2,4-dioxopiperidine | AA |
| 11. 1-Benzyl-3-(1,3-dithiolan-2-ylidene)-2,4-dioxopiperidine | AA |
| 12. 1-(3-Pyridylmethyl)-3-(1,3-dithiol-2-ylidene)-2,4-dioxopiperidine | AA |
| 13. 1-Phenyl-3-(1,3-dithiol-2-ylidene)-2,4-dioxopiperidine | AA |

TABLE 2-continued

| Test compound Nos. and chemical names | Evaluation (Dose: 100 mg/kg × 2) |
|---|---|
| 14. 1-Benzyl-3-(1,3-dithiol-2-ylidene)-5-methyl-2,4-dioxopiperidine | AA |
| 15. 1-Benzyl-3-(1,3-dithiol-2-ylidene)-5-ethyl-2,4-dioxopiperidine | AA |
| 16. 1-Benzyl-5-(1,3-dithiol-2-ylidene)-4,6-dioxopiperidine-2,3-dicarboxylic acid diethyl ester | AA |
| 17. Ethyl 2-(1,3-dithiol-2-ylidene)-2-(N—benzylcarbamoyl)acetate | AA |

EXPERIMENT 2

Activity against subacute hepatic damage induced by carbon tetrachloride:

Method: A solution of carbon tetrachloride in olive oil was subcutaneously administered to SD male rats (age: 6 weeks old, weight: 170–210 g, one group: 5 rats) in a dose of 1 ml/kg (carbon tetrachloride: 0.5 ml/kg) once a day for 4 days continuously. At the same time, a suspension of a test compound in a 0.5% carboxymethyl cellulose solution (test compound: 100 mg/10 ml/kg) was orally administered once a day for four days. Twenty-four hours after the last administration of a suspension of test compound, blood was collected from the inferior vena cava. Immediately, the liver was taken out. The plasma was isolated from the blood, and activities of GPT and GOT in the plasma were measured. Triglyceride (TG) content in the liver was also determined. As the normal control, olive oil and the 0.5% carboxymethyl cellulose solution were administered to the animals instead of the solution of carbon tetrachloride and the suspension of test compound. Besides, the CCl₄-control group was given the CCl₄ solution and the 0.5% carboxymethyl cellulose solution.

The test results are shown in Table 3.

TABLE 3

| | Test compound* group Comp. No. 6 | CCl₄— control group | Normal control group |
|---|---|---|---|
| GPT (K.U.) | 22.0 ± 1.6 | 110.2 ± 26.2 | 18.6 ± 1.4 |
| GOT (K.U.) | 69.0 ± 3.4 | 203.8 ± 34.2 | 59.8 ± 5.0 |
| TG (mg/g) | 6.4 ± 0.7 | 36.0 ± 4.1 | 7.3 ± 0.5 |

*The test compound No. 6: The same as in Experiment 1

EXAMPLE 1

(1) A mixture of 2,4-dioxopiperidine (15.1 g), methyl orthoformate (30 ml) and p-toluenesulfonic acid (3.0 g) in methanol (300 ml) is refluxed for 1 hour. After evaporating the solvent, the residue is dissolved in benzene and refluxed for 5 hours. To the solution is added potassium carbonate (9.0 g), and the mixture is stirred overnight at room temperature and then filtered. The filtrate is distilled to remove the solvent. The residue is recrystallized from ethyl acetate-isopropyl alcohol to give 4-methoxy-5,6-dihydro-2(1H)-pyridone (12.3 g, 72.5%) as colorless prisms. m.p. 115°–117° C.

(2) Sodium hydride (in the form of a 60% dispersion in oil) (447 mg) is suspended in N,N-dimethylformamide (10 ml), and thereto is added dropwise a solution of 4-methoxy-5,6-dihydro-2(1H)-pyridone (1.29 g) in N,N-dimethylformamide (30 ml). The mixture is stirred under ice-cooling for 30 minutes, and thereto is added dropwise ethyl iodide (0.97 ml). The mixture is stirred under ice-cooling for 30 minutes and further at room temperature for 2.5 hours. The reaction mixture is poured onto water and extracted with chloroform. The extract is washed with a saturated sodium chloride solution and dried. After evaporating the solvent, the residue is dissolved in ethanol (120 ml) and thereto is added 10% hydrochloric acid (60 ml), and the mixture is allowed to stand at 25° C. for 5 hours. After distilling off the solvent under reduced pressure, the residue is dissolved in chloroform, washed with 5% aqueous sodium hydrogen carbonate solution and water, and then dried. The solvent is distilled off to give 1-ethyl-2,4-dioxopiperidine (1.12 g, 78%).

(3) 1-Ethyl-2,4-dioxopiperidine (1.06 g) is dissolved in N,N-dimethylformamide (50 ml), and the solution is added dropwise to a suspension of sodium hydride (60% dispersion in oil, 332 mg) in N,N-dimethylformamide (50 ml) under ice-cooling. The mixture is stirred for 20 minutes, and thereto is added 2-methylthio-1,3-dithiolium iodide (1.89 g). After stirring at room temperature overnight, the reaction mixture is poured onto water and extracted with ethyl acetate. The extract is washed with water, dried and distilled to remove the solvent. The residue is purified by silica gel column chromatography (developer: ethyl acetate) and then recrystallized from ethyl acetate-isopropyl ether to give 1-ethyl-3-(1,3-dithiol-2-ylidene)-2,4-dioxopiperidine (1.10 g) as pale yellow needles. m.p. 114.5°–117° C.

IR$\nu_{max}^{KBr}$ (cm$^{-1}$): 1585, 1620.

NMR (CDCl$_3$)δ: 1.21 (t, J=7.2 Hz, 3H), 3.58 (q, J=7.2 Hz, 2H), 7.28 (s, 2H).

EXAMPLES 2–9

(1) In the same manner as described in Example 1-(2), the corresponding starting materials are treated to give the compounds (III-d) as shown in Table 4. The compounds thus obtained are all crude product, but they are used as they stand, i.e. without purifying, in the subsequent step.

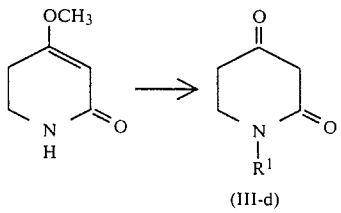

(III-d)

TABLE 4

| Ex. No. | Compound (III-d) R$^1$ | Yield |
|---|---|---|
| 2 | n-Butyl | Yield: 93% |
| 3 | n-Hexyl | Yield: 79.3% |
| 4 | n-Octyl | Yield: quantitative |
| 5 | n-Decyl | Yield: quantitative |
| 6 | Allyl | Yield: quantitative |
| 7 | 4-Methylbenzyl | Yield: quantitative |
| 8 | 3,4-Dichlorobenzyl | Yield: quantitative |
| 9 | 3,4-Dimethoxybenzyl | Yield: 65.2% |

(2) In the same manner as described in Example 1-(3), the compounds obtained in the above (1) are each treated to give the compounds (I-j) as shown in Table 5.

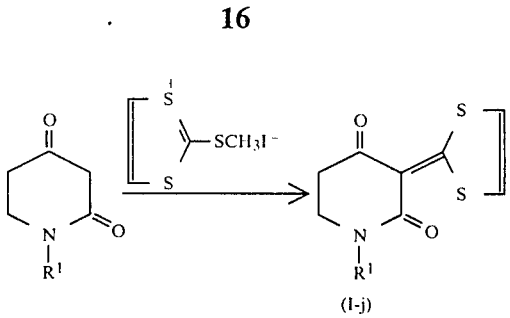

(I-j)

TABLE 5

| Ex. No. | Compound (I-j) R$^1$ | Properties, etc. |
|---|---|---|
| 2 | n-Butyl | Pale yellow needles, m.p. 102–104° C. (recrystallized from ethyl acetate-n-hexane), IR$\nu_{max}^{KBr}$ (cm$^{-1}$): 1590, 1625 NMR (CDCl$_3$)δ: 0.96 (m, 3H), 7.27 (s, 2H) |
| 3 | n-Hexyl | Pale yellow needles, m.p. 88–89.5° C. (recrystallized from ethyl acetate-n-hexane), IR$\nu_{max}^{KBr}$ (cm$^{-1}$): 1595, 1625 NMR (CDCl$_3$)δ: 0.89 (m, 3H), 7.24 (s, 2H) |
| 4 | n-Octyl | Pale yellow needles, m.p. 86–87.5° C. (recrystallized from ethyl acetate-n-hexane), IR$\nu_{max}^{KBr}$ (cm$^{-1}$): 1590, 1620 NMR (CDCl$_3$)δ: 0.86 (m, 3H), 7.25 (s, 2H) |
| 5 | n-Decyl | Pale yellow needles, m.p. 93.5–94.5° C. (recrystallized from ethyl acetate-n-hexane), IR$\nu_{max}^{KBr}$ (cm$^{-1}$): 1590, 1620 NMR (CDCl$_3$)δ: 0.87 (m, 3H), 7.25 (s, 2H) |
| 6 | Allyl | Pale yellow needles, m.p. 133–134.5° C. (recrystallized from ethyl acetate-n-hexane), IR$\nu_{max}^{KBr}$ (cm$^{-1}$): 1590, 1620 NMR (CDCl$_3$)δ: 5.0–5.15 (m, 1H), 5.25–5.4 (m, 1H), 5.5–6.3 (m, 1H), 7.28 (s, 2H) |
| 7 | 4-Methylbenzyl | Pale yellow needles, m.p. 137–138° C. (recrystallized from isopropyl alcohol), IR$\nu_{max}^{KBr}$ (cm$^{-1}$): 1590, 1625 NMR (CDCl$_3$)δ: 2.31 (s, 3H), 4.68 (s, 2H), 7.25 (s, 2H) |
| 8 | 3,4-Dichlorobenzyl | Pale yellow needles, m.p. 175–176.5° C. (recrystallized from ethyl acetate), IR$\nu_{max}^{KBr}$ (cm$^{-1}$): 1590, 1625 NMR (CDCl$_3$)δ: 4.69 (s, 2H), 7.34 (s, 2H) |
| 9 | 3,4-dimethoxybenzyl | Pale yellow needles, m.p. 195–196.5° C. (recrystallized from ethyl acetate-n-hexane), IR$\nu_{max}^{KBr}$ (cm$^{-1}$): 1590, 1625 NMR (CDCl$_3$)δ: 3.86 (s, 6H), 4.68 (s, 2H), 7.35 (s, 2H) |

EXAMPLE 10

Sodium hydride (60% dispersion in oil) (80 mg) is suspended in tetrahydrofuran (10 ml), and thereto are added 1-benzyl-2,4-dioxopiperidine (200 mg) and 2-methylthio-1,3-dithiolium iodide (273 mg). The mixture is stirred at room temperature for 30 minutes. The reaction mixture is poured onto water and extracted with chloroform. The extract is washed with a saturated sodium chloride solution, dried and then distilled to remove the solvent. The residue is purified by silica gel column chromatography (solvent; ethyl acetate:n-hexane=1:1) and recrystallized from isopropyl alcohol to give 1-benzyl-3-(1,3-dithiol-2-ylidene)-2,4-dioxopiperidine (262 mg, 87.8%) as pale yellow needles, m.p. 122°-124° C.

IR$\nu_{max}^{chloroform}$ (cm$^{-1}$): 1590, 1630.

NMR (CDCl$_3$)δ: 4.75 (s, 2H), 7.29 (s, 8H).

EXAMPLE 11

(1) Phenethylamine (121 g) is dissolved in methanol (500 ml) and thereto is added dropwise methyl acrylate (86 g) at room temperature. The mixture is stirred for 4 hours and then distilled to remove the solvent to give N-phenethyl-β-alanine methyl ester (157.8 g, 76%), b.p. 124°-127° C. (1.2 mmHg).

(2) N-Phenethyl-β-alanine methyl ester (80.2 g) is dissolved in methanol (150 ml), and thereto is added dropwise diketene (32 ml) under ice-cooling. The mixture is stirred at room temperature for 1 hour and then distilled to remove the solvent. The residue is dissolved in methanol (100 ml), and the solution is added dropwise to a solution of sodium methoxide [prepared from metal sodium (9.8 g) and methanol (150 ml)], and the mixture is stirred at room tempeature for 2 hours. After the reaction, the solvent is distilled off, and to the residue is added ice-water. The mixture is extracted with ethyl acetate, and the aqueous layer is acidified with conc. hydrochloric acid and then is extracted with ethyl acetate. The ethyl acetate extract is washed with water, dried and then distilled to remove the solvent to give 1-phenethyl-3-acetyl-2,4-dioxopiperidine (95.3 g, 95%) as a colorless oily substance.

(3) 1-Phenethyl-3-acetyl-2,4-dioxopiperidine (5.0 g) and 10% hydrochloric acid (30 ml) are added to ethanol (50 ml), and the mixture is refluxed for 6 hours. After distilling off the solvent, the residue is dissolved in chloroform, and the solution is washed with a saturated sodium chloride solution, dried and then distilled to remove the solvent to give 1-phenethyl-2,4-dioxopiperidine (3.62 g, 86.4%) as an oily substance.

(4) The 1-phenethyl-2,4-dioxopiperidine obtained in the above (3) is treated in the same manner as described in Example 10 to give the compound (I-j) as shown in Table 6.

TABLE 6

| Compound (I-j) R$^1$ | Properties, etc. |
| --- | --- |
| Phenethyl | Pale yellow needles, m.p. 147–148° C. (recrystallized from isopropyl alcohol), IR$\nu_{max}^{KBr}$(cm$^{-1}$): 1585, 1625 NMR (CDCl$_3$)δ: 7.24 (s, 7H) |

EXAMPLE 12

(1) 2,4-Dioxohexahydroazepine (4.57 g), methyl orthoformate (8.15 g) and p-toluenesulfonic acid (215 mg) are treated in the same manner as described in Example 1-(1) to give 4-methoxy-2,4,6,7-tetrahydroazepine-2-one (3.24 g, 63.8%) as colorless prisms. m.p. 70°-73° C.

(2) 4-Methoxy-2,5,6,7-tetrahydroazepine-2-one (1.20 g) is treated in the same manner as described in Example 1-(2) to give 1-benzyl-2,4-dioxohexahydroazepine (1.145 g, 60.2%) as an oil.

IR$\nu_{max}^{CHCl_3}$ (cm$^{-1}$): 1645, 1710.

NMR (CDCl$_3$)δ: 4.63 (s, 2H).

(3) The 1-benzyl-2,4-dioxohexahydroazepine obtained in the above (2) is treated in the same manner as described in Example 10 to give the compound (I) as shown in Table 7.

TABLE 7

| Compound (I) | | | | |
| --- | --- | --- | --- | --- |
| R$^1$ | R$^2$, R$^3$ | R$^4$ | A | Properties, etc. |
| Benzyl | —CH=CH— | H | —(CH$_2$)$_2$— | Pale yellow needles, m.p. 178–181° C. (recrystallized from isopropyl alcohol), IR$\nu_{max}^{KBr}$(cm$^{-1}$): 1580, 1615 NMR (CDCl$_3$)δ: 4.78 (s, 2H), 7.14 (s, 2H), 7.33 (s, 5H) |

EXAMPLE 13

Sodium hydride (60% dispersion in oil) (83 mg) is suspended in dimethoxyethane (10 ml), and to the suspension is added 2,4-dioxopiperidine (200 mg). The mixture is stirred at room temperature for 10 minutes and thereto is added 2-methylthio-1,3-dithiolium iodide (489 mg). The mixture is stirred at 50° C. for 2.5 hours and then is added additional 2-methylthio-1,3-dithiolium iodide (49 mg). The mixture is stirred at 50° C. for 2.5 hours. After distilling off the solvent under reduced pressure, water is added to the residue. The mixture is extracted with chloroform and the extract is washed with a saturated sodium chloride solution and dried. After distilling off the solvent, the residue is recrystallized from methanol to give 3-(1,3-dithiol-2-ylidene)-2,4-dioxopiperidine (284 mg, 75%) as pale yellow needles. m.p. 277°-279° C.

IR$\nu_{max}^{CHCl_3}$ (cm$^{-1}$): 1600, 1640.

NMR (CDCl$_3$)δ: 7.31 (s, 2H).

EXAMPLE 14

Sodium hydride (60% dispersion in oil) (226 mg) is suspended in N,N-dimethylformamide (10 ml), and to the suspension is added dropwise a solution of 3-(1,3-dithiol-2-ylidene)-2,4-dioxopiperidine (1.0 g) (which is prepared in Example 13) in N,N-dimethylformamide (100 ml) while cooling at 0° to 5° C. The mixture is stirred for 10 minutes at the same temperature, and to the mixture is added dropwise methyl iodide (861 mg), and the mixture is stirred at 0° to 2° C. for 1.5 hour. After distilling off the solvent under reduced pressure, the residue is purified by silica gel column chromatography (solvent, n-hexane:ethyl acetate=1:1), and recrystallized from ethyl acetate-isopropyl ether to give 1-methyl-3-(1,3-dithiol-2-ylidene)-2,4-dioxopiperidine (634 mg, 59.5%) as pale yellow needles. m.p. 148.5°-153° C.

IR$\nu_{max}^{CHCl_3}$ (cm$^{-1}$): 1595, 1630.

NMR (CDCl$_3$)δ: 3.11 (s, 3H), 7.28 (s, 2H).

EXAMPLES 15 AND 16

3-(1,3-Dithiol-2-ylidene)-2,4-dioxopiperidine as prepared in Example 13 is reacted with the corresponding starting material in the same manner as described in Example 14 to give the compounds (I-j) as shown in Table 8.

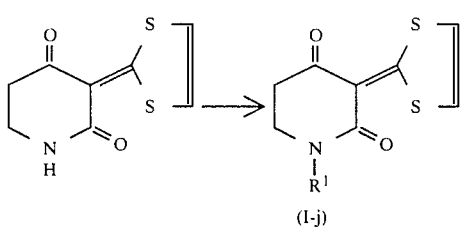

(I-j)

TABLE 8

| Ex. No. | Compound (I-j) R¹ | Properties, etc. |
|---|---|---|
| 15 | 4-Chloro benzyl | Pale yellow needles, m.p. 143–149° C. (recrystallized from ethanol), IR$\nu_{max}^{chloroform}$ (cm$^{-1}$): 1585, 1620 NMR (CDCl$_3$)δ: 4.72 (s, 2H), 7.28 (s, 4H), 7.32 (s, 2H) |
| 16 | 4-Methoxy-benzyl | Pale yellow needles m.p. 160–162° C. (recrystallized from ethyl acetate-isopropyl ether), IR$\nu_{max}^{chloroform}$ (cm$^{-1}$): 1585, 1625 NMR (CDCl$_3$)δ: 3.77 (s, 3H), 4.67 (s, 2H), 7.28 (s, 2H) |

EXAMPLE 17

Sodium hydride (60% dispersion in oil) (47 mg) is suspended in N,N-dimethylformamide (2 ml), and to the suspension is added dropwise a solution of 3-(1,3-dithiol-2-ylidene)-2,4-dioxopiperidine (200 mg) in N,N-dimethylformamide (16 ml). The mixture is stirred for 10 minutes and thereto is added benzyl bromide (0.12 ml), and the mixture is further stirred for 1 hour. After the reaction, the reaction mixture is distilled to remove the solvent under reduced pressure and the residue is dissolved in chloroform. The chloroform solution is washed with an aqueous saturated sodium chloride solution, dried and then distilled to remove the solvent. The residue is recrystallized from isopropyl alcohol to give 1-benzyl-3-(1,3-dithiol-2-ylidene)-2,4-dioxopiperidine (176 mg, 62%) as pale yellow needles. m.p. 122°–124° C.

EXAMPLE 18

1-Benzyl-2,4-dioxopiperidine (2.03 g) and carbon disulfide (760 mg) are dissolved in dimethylsulfoxide (20 ml), and thereto is added dropwise a solution of potassium hydroxide (1.1 g) in water (3 ml) at room temperature. The mixture is stirred for 30 minutes and thereto is added dropwise a solution of 1,2-dibromomethane (1.87 g) in dimethylsulfoxide (3 ml). The mixture is stirred at room temperature for 2 hours and further at 60° C. for 1 hour. The reaction mixture is poured onto water and extracted with benzene-ethyl acetate. The extract is washed with water, dried and distilled to remove the solvent. The residue is purified by silica gel column chromatography (solvent, benzene:ethyl acetate=8:2) and is recrystallized from ethanol to give 1-benzyl-3-(1,3-dithiolan-2-ylidene)-2,4-dioxopiperidine (1.08 g) as pale yellow needles. m.p. 148°–150° C.

IR$\nu_{max}^{nujol}$ (cm$^{-1}$): 1609, 1649.

NMR (CDCl$_3$)δ: 3.33 (s, 4H), 4.73 (s, 2H), 7.30 (s, 5H).

EXAMPLE 19

In the same manner as described in Example 18, the corresponding starting materials are treated to give the compounds (I) as shown in Table 9.

TABLE 9

| Compound (I) | | | | | |
|---|---|---|---|---|---|
| R¹ | R² | R³ | R⁴ | A | Properties, etc. |
| Benzyl | CH$_3$ | CH$_3$ | H | —CH$_2$— | Pale yellow oil (yield: 59.3%) IR$\nu_{max}^{chloroform}$ (cm$^{-1}$): 1620, 1655 NMR (CDCl$_3$)δ: 2.50 (s, 6H), 4.71 (s, 2H), 7.29 (s, 5H) |

EXAMPLE 20

(1) N-Benzylglycine methyl ester hydrochloride (23.0 g) is dissolved in ethanol (180 ml) and thereto is added triethylamine (11.1 g) under ice-cooling and further added dropwise diketene (9.2 g). The mixture is stirred at room temperature for 1 hour and distilled to remove the solvent. The residue is dissolved in chloroform, washed with water, 10% hydrochloric acid, and water in this order, dried and then distilled to remove the solvent. The residue is dissolved in xylene (360 ml) and the solution is added dropwise to a solution of sodium methoxide [which is prepared from metal sodium (2.6 g) and methanol (180 ml)], and the mixture is stirred at 80° C. for 2.5 hours while distilling off methanol. After cooling, the reaction mixture is extracted with water. The extract is acidified with 10% hydrochloric acid and extracted with ethyl acetate. The ethyl acetate extract is washed with water, dried and distilled to remove the solvent. The residue is recrystallized from n-hexane-isopropyl ether-diethyl ether to give 1-benzyl-3-acetyl-2,4-dioxopyrrolidine (20.33 g, 87.7%). m.p. 74°–75° C.

The product obtained above (6.94 g) and 5% hydrochloric acid (60 ml) are added to ethanol (40 ml), and the mixture is refluxed for 6.5 hours. The reaction mixture is distilled under reduced pressure to remove the solvent. To the residue is added ice-water, and the mixture is saturated with sodium chloride and extracted with ethyl acetate. The extract is washed with an aqueous saturated sodium chloride solution, dried and then distilled to remove the solvent to give 1-benzyl-2,4-dioxopyrrolidine (4.57 g, 80.5%) as an oily substance.

IR$\nu_{max}^{liquid}$ (cm$^{-1}$): 1685, 1765.

(2) The 1-benzyl-2,4-dioxopyrrolidine obtained in the above (1) and the corresponding starting material is reacted in the same manner as described in Example 18 to give the compound (I) as shown in Table 10.

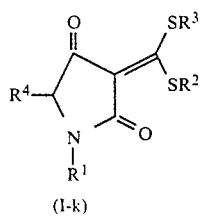

(I-k)

TABLE 10

| Compound (I-k) | | | | |
|---|---|---|---|---|
| $R^1$ | $R^2$, $R^3$ | $R^4$ | Properties, etc. | |
| Benzyl | —CH=CH— | H | Pale yellow needles m.p. 186–186.5° C. (recrystallized from isopropyl alcohol) $IR\nu_{max}^{nujol}$ (cm$^{-1}$): 1635, 1685 NMR (CDCl$_3$)δ: 3.72 (s, 2H), 4.69 (s, 2H), 7.29 (s, 7H) | |

EXAMPLE 21

Sodium hydride (60% despersion in oil) (432 mg) is suspended in dimethylsulfoxide (10 ml), and to the suspension is added dropwise a solution of 1-benzyl-2,4-dioxopiperidine (1.0 g) and carbon disulfide (0.33 ml) in dimethylsulfoxide (20 ml). The mixture is stirred for 2 hours, and thereto is added dropwise a solution of cis-1,2-dichloroethylene (0.42 ml) in dimethylsulfoxide (5 ml). The mixture is stirred at room temperature for 1.5 hour and further at 50° C. for 1 hour. The reaction mixture is poured onto water and extracted with benzene. The extract is washed with water, dried and then distilled to remove the solvent. The residue is recrystallized from isopropyl alcohol to give 1-benzyl-3-(1,3-dithiol-2-ylidene)-2,4- dioxopiperidine (486 mg) as pale yellow needles. m.p. 122°–124° C.

EXAMPLE 22

(1) A mixture of benzylamine (43.24 g) and methylene chloride (300 ml) is cooled with ice-water, and a solution of ethoxycarbonylacetyl chloride (29.63 g) in methylene chloride (150 ml) is added dropwise thereto. The mixture is stirred at the same temperature for 2 hours. The mixture is filtered to remove precipitates (benzylamine hydrochloride). The filtrate is washed with 2% hydrochloric acid and a saturated sodium chloride solution, dried and then evaporated to remove the solvent. The residue is recrystallized from a mixture of ether and n-hexane, whereby ethyl (N-benzylcarbamoyl)acetate (42.15 g) is obtained as colorless needles. Yield: 96.8%.
M.p. 50°–52° C.
IR$\nu_{max}^{KBr}$ (cm$^{-1}$): 1735, 1650.
NMR (CDCl$_3$)δ: 3.34 (s, 2H, —COCH$_2$CO—), 4.47(d, J=5.7 Hz, 2H,

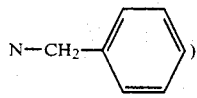

Mass (m/e): 221 (M+).

(2) Ethyl (N-benzylcarbamoyl)acetate (39.00 g) and carbon disulfide (14.03 g) are dissolved in dimethylsulfoxide (390 ml). A solution of potassium hydroxide (21.52 g) in water (39 ml) is added dropwise to the mixture at 20° to 40° C. The mixture is stirred at the same temperature for 30 minutes, and then cis-1,2-dichloroethylene (17.84 g) is added dropwise thereto. The mixture is stirred at 50° C. for 5 hours. Cis-1,2-dichloroethylene (3.24 g) is further added to the mixture 3 hours after the commencement of the reaction. After cooling, the mixture is poured into water, and the aqueous solution is extracted with ethyl acetate. The extract is washed with water, dried and then evaporated to remove the solvent. The residue is purified by silica gel column chromatography (solvent: n-hexane-ethyl acetate=2:1), and then recrystallized from a mixture of n-hexane and ethyl acetate, whereby ethyl 2-(1,3-dithiol-2-ylidene)-2-(N-benzylcarbamoyl)acetate (33.77 g) is obtained as pale yellow prisms. Yield: 62.8%.
M.p 78.5°–80.5° C.
IR$\nu_{max}^{KBr}$(cm$^{-1}$): 1665, 1600.
NMR(CDCl$_3$)δ: 7.07 (s, 2H,

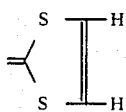

Mass (m/e): 321 (M+).

(3) Sodium hydride (a 60% dispersion in oil) (1.50 g) is suspended in N,N-dimethylformamide (100 ml) and a solution of ethyl 2-(1,3-dithiol-2-ylidene)-2-(N-benzylcarbamoyl)acetate (10.0 g) in dimethylformamide (250 ml) is added dropwise thereto at 4° to 5° C. The mixture is stirred at the same temperature for 30 minutes. A solution of ethyl acrylate (4.1 ml) in dimethylformamide (100 ml) is added dropwise to the mixture, and the mixture is stirred at the same temperature for one hour and then at room temperature for 5 hours. The mixture is poured into ice-water, and the aqueous solution is extracted with ethyl acetate. The extract is washed with water, dried and then evaporated to remove the solvent. The residue is recrystallized from a mixture of n-hexane and ethyl acetate, whereby ethyl 1-benzyl-5-(1,3-dithiol-2-ylidene)-4,6-dioxopiperidine-3-carboxylate (8.76 g ) is obtained as pale yellow needles. Yield: 75%.
M.p. 127°–129° C.
IR$\nu_{max}^{CHCl_3}$ (cm$^{-1}$): 1730, 1630, 1595.
NMR (CDCl$_3$)δ: 4.83 (d, J=15 Hz, 1H,

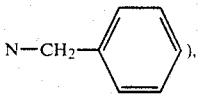

4.63 (d, J=15 Hz, 1H,

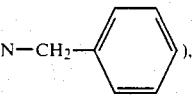

7.32 (s, 2H,

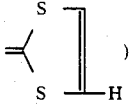

Mass (m.e): 375 (M+).

EXAMPLE 23

Sodium hydride (a 60% of dispersion in oil) (189 mg) is suspended in 1,2-dimethoxyethane (20 ml), and the mixture is cooled with ice-water. A solution of ethyl (N-benzylcarbamoyl)acetate (1.002 g) in 1,2-dimethoxyethane (23 ml) is added dropwise to the mixture. The mixture is stirred for 30 minutes. Then, 2-methylthio-1,3-dithiolium iodide (1.309 g) is added to the mixture, and the mixture is stirred at room temperature for 2 hours and then at 40° C. to 50° C. for one hour. After cooling, the mixture is poured into ice-water, and the aqueous solution is extracted with ethyl acetate. The extract is washed with water, dried and then evaporated to remove the solvent. The residue thus obtained is treated in the same manner as described in Example 22-(2), whereby ethyl 2-(1,3-dithiol-2-ylidene)-2-(N-benzylcarbamoyl)acetate (595 mg) is obtained.

M.p. 79°–81° C.

IR, NMR and Mass spectrum of this product are identified with those of the sample obtained in Example 22-(2). This product is treated in the same manner as described in Example 22-(3), whereby ethyl 1-benzyl-5-(1,3-dithiol-2-ylidene)-4,6-dioxopiperidine-3-carboxylate is obtained.

EXAMPLE 24

Ethyl 1-benzyl-5-(1,3-dithiol-2-ylidene)-4,6-dioxopiperidine-3-carboxylate (2.0 g) is dissolved in ethanol (160 ml), and a 10% aqueous sodium hydroxide solution (8.0 ml) is added thereto. The mixture is refluxed for 2 hours. The mixture is cooled, neutralized with 10% hydrochloric acid, and then evaporated under reduced pressure to remove the solvent. The residue is dissolved in ethyl acetate, and the solution is washed with water, dried and then evaporated to remove the solvent. The residue thus obtained is recrystallized from isopropanol, whereby 1-benzyl-3-(1,3-dithiol-2-ylidene)-2,4-dioxopiperidine (1.26 g) is obtained as pale yellow needles. Yield: 78%.

M.p. 123°–124° C.
IR$\nu_{max}^{CHCl_3}$ (cm$^{-1}$): 1630, 1590.
NMR (CDCl$_3$)δ: 4.75 (s, 2H,

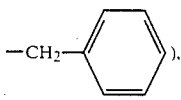

), 7.29 (s, 8H,

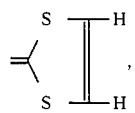

benzene ring )
Mass (m/e): 303 (M+).

EXAMPLE 25

(1) Sodium hydride (60% dispersion in oil, 175 mg) is suspended in dimethylformamide (10 ml), and thereto is added dropwise a solution of ethyl 1-benzyl-5-(1,3-dithiol-2-ylidene)-4,6-dioxopiperidine-3-carboxylate (1.3 g) in dimethylformamide (30 ml) under ice-cooling. The mixture is stirred at the same temperature for 20 minutes. Methyl iodide (0.7 ml) is added to the mixture, and the mixture is stirred under ice-cooling for 1.5 hours and then at room temperature for 1.5 hours. The mixture is poured into water and extracted with ethyl acetate. The extract is washed with a saturated sodium chloride solution, dried and then distilled to remove the solvent. The residue is recrystallized from a mixture of ethyl acetate and n-hexane to give ethyl 1-benzyl-5-(1,3-dithiol-2-ylidene)-3-methyl-4,6-dioxopiperidine-3-carboxylate (1.15 g, 85.2%) as pale yellow needles, m.p. 111°–113° C.

IR$\nu_{max}^{KBr}$ (cm$^{-1}$): 1725, 1625, 1595.
NMR (CDCl$_3$)δ: 1.39 (s, 3H).

(2) Ethyl 1-benzyl-5-(1,3-dithiol-2-ylidene)-3-methyl-4,6-dioxopiperidine-3-carboxylate (245 mg) is dissolved in ethanol (5 ml), and thereto is added a 10% sodium hydroxide solution (2.5 ml). The mixture is stirred at room temperature overnight. The mixture is acidified with 10% HCl, and poured into water. The aqueous solution is extracted with ethyl acetate. The extract is washed with a saturated sodium chloride solution, dried and then distilled to remove the solvent. The residue is dissolved in ethanol (20 ml) and the solution is refluxed for one hour. The mixture is distilled to remove the solvent. The residue is purified by silica gel column chromatography (solvent, ethyl acetate:n-hexane=1:1), and is recrystallized from a mixture of ethyl acetate and n-hexane to give 1-benzyl-3-(1,3-dithiol-2-ylidene)-5-methyl-2,4-dioxopiperidine (138 mg, 69.1%) as pale yellow needles, m.p. 168°–170° C.

IR$\nu_{max}^{KBr}$ (cm$^{-1}$): 1625, 1585.
NMR (CDCl$_3$)δ: 1.18 (d, J=6.4 Hz, 3H), 4.76 (d, J=15 Hz, 1H), 4.81 (d, J=15 Hz, 1H), 7.35 (s, 7H).

EXAMPLE 26

(1) Ethyl 1-benzyl-5-(1,3-dithiol-2-ylidene)-4,6-dioxopiperidine-3-carboxylate (2.70 g) and ethyl iodide (0.71 ml) are treated in the same manner as described in Example 25-(1), whereby ethyl 1-benzyl-5-(1,3-dithiol-2-ylidene)-3-ethyl-4,6-dioxopiperidine-3-carboxylate (2.30 g, 79.3%) is obtained as pale yellow oil.

IR$\nu_{max}^{chloroform}$ (cm$^{-1}$): 1725, 1625, 1595.
NMR (CDCl$_3$)δ: 0.89 (t, J=7.3 Hz, 3H).

(2) Ethyl 1-benzyl-5-(1,3-dithiol-2-ylidene)-3-ethyl-4,6-dioxopiperidine-3-carboxylate (710 mg) is treated in the same manner as described in Example 25-(2), whereby 1-benzyl-3-(1,3-dithiol-2-ylidene)-5-ethyl-2,4-dioxopiperidine (455 mg, 78%) is obtained as pale yellow needles, m.p. 139.5°–141° C.

IR$\nu_{max}^{KBr}$ (cm$^{-1}$): 1625, 1590.
NMR (CDCl$_3$)δ: 0.83 (t, J=7.2 Hz, 3H), 4.69 (d, J=15 Hz, 1H), 4.81 (d, J=15 Hz, 1H), 7.28 (s, 2H).

EXAMPLE 27

(1) 3-Pyridylmethylamine (10.81 g) is dissolved in methanol (50 ml), and thereto is added dropwise methyl acrylate (8.60 g) under ice-cooling. The mixture is stirred at room temperature for 18 hours. The mixture is distilled to remove the solvent, and then the residue is distilled under reduced pressure to give methyl 3-(3-pyridylmethylamino)propionate (16.02 g, 82.5%), b.p. 119°–120° C./0.4 mmHg.

(2) A mixture of methyl 3-(3-pyridylmethylamino)propionate (28.72 g), triethylamine (22 ml) and methylene chloride (240 ml) is cooled to 5°–10° C., and thereto is added dropwise a solution of ethoxycarbonylacetyl chloride (23.38 g) in methylene chloride (60 ml). The mixture is stirred at room temperature for one hour. The mixture is filtered to remove precipitates (triethylamine hydrochloride). The filtrate is washed with water, dried and then distilled to remove the solvent. The residue is purified by silica gel column chromatography (solvent, ethyl acetate) to give ethyl[N-(3-pyridylmethyl)-N-(methoxycarbonylethyl)carbamoyl]acetate (35.22 g, 77.3%) as oil.

IR$\nu_{max}^{liquid}$ (cm$^{-1}$): 1730, 1645.
Mass (m/e)δ: 308 (M+).

(3) Ethyl[N-(3-pyridylmethyl)-N-(methoxycarbonylethyl)carbamoyl]acetate (1.0 g) and carbon disulfide (0.2 ml) are dissolved in dimethylsulfoxide (12 ml), and thereto is added a solution of potassium hydroxide (378 mg) in water (1 ml). The mixture is stirred at room temperature for 20 minutes. A solution of cis-1,2-dichloroethylene (0.245 ml) in dimethylsulfoxide (2 ml) is added dropwise to the mixture, and the mixture is stirred at 50°–55° C. for 6 hours. After cooling, the mixture is poured into water, and the aqueous solution is extracted with ethyl acetate. The extract is washed with water, dried and then distilled to remove the solvent. The residue is purified by silica gel column chromatography (solvent, ethyl acetate) to give ethyl 2-(1,3-dithiol-2-ylidene)-2-[N-(3-pyridylmethyl)-N-(methoxycarbonylethyl)carbamoyl]acetate (429 mg) as oil.

IR$\nu_{max}^{liquid}$ (cm$^{-1}$): 1730, 1655, 1620.

Mass (m/e)δ: 408 (M+).

(4) Sodium (156 mg) is added to methanol (5ml) and thereto is added a solution of ethyl 2-(1,3-dithiol-2-ylidene)-2-[N-(3-pyridylmethyl)-N-(methoxycarbonylethyl)carbamoyl]acetate (2.21 g) in benzene (35 ml). The mixture is refluxed for 3 hours, and distilled to remove the solvent. The residue is dissolved in ethyl acetate, and the solution is washed with water, dried and then distilled to remove the solvent. The residue is recrystallized from a mixture of ethyl acetate and n-hexane to give methyl 1-(3-pyridylmethyl)-5-(1,3-dithiol-2-ylidene)-4,6-dioxopiperidine-3-carboxylate (1.0 g, 51%) as pale yellow needles, m.p. 111°–114° C.

IR$\nu_{max}^{nujol}$ (cm$^{-1}$): 1740, 1620, 1585.

NMR (CDCl$_3$)δ: 3.69 (s, 3H), 4.76 (s, 2H), 7.39 (s, 2H).

The compound obtained above is treated with HCl-ether to give the corresponding hydrochloride as yellow needles.

m.p. 204°–205.5° C. (recrystallized from methanol).

EXAMPLE 28

Methyl 1-(3-pyridylmethyl)-5-(1,3-dithiol-2-ylidene)-4,6-dioxopiperidine-3-carboxylate (244 mg) obtained in Example 27 is dissolved in methanol (15 ml), and thereto is added a 10% sodium hydroxide solution (2 ml). The mixture is refluxed for 2 hours. The mixture is poured into water, and extracted with chloroform. The extract is washed with water, dried and then distilled to remove the solvent. The residue is recrystallized from a mixture of ethyl acetate and and n-hexane to give 1-(3-pyridylmethyl)-3-(1,3-dithiol-2-ylidene)-2,4-dioxopiperidine (114 mg, 66.1%) as yellow plates, m.p. 131.5°–133° C.

IR$\nu_{max}^{nujol}$ (cm$^{-1}$): 1620, 1590.

NMR (CDCl$_3$)δ: 4.75 (s, 2H), 7.31 (s, 2H).

The compound obtained above is treated with HCl-ether to give the corresponding hydrochloride as pale yellow needles.

m.p. 243.5° C. (decomp., recrystallized form methanol).

EXAMPLE 29

(1) Sodium (0.77 g) is dissolved in methanol (30 ml), and thereto is added dropwise a solution of ethyl [N-(3-pyridylmethyl)-N-(methoxycarbonylethyl)carbamoyl]acetate (10.0 g) in benzene (170 ml) at 3°–8° C. The mixture is stirred at the same meperature for 2 hours. The mixture is distilled to remove the solvent, and the residue is dissolved in water. The aqueous solution is extracted with benzene, and the aqueous layer is neutralized with 10% HCl, and extracted with chloroform. The extract is dried and distilled to remove the solvent to give methyl 1-(3-pyridylmethyl)-2,4-dioxopiperidine-3-carboxylate (8.50 g, quantitative) as oil.

IR$\nu_{max}^{liquid}$ (cm$^{-1}$): 1720, 1650, 1590.

NMR (CDCl$_3$)δ: 3.90 (s, 3H), 4.61 (s, 2H).

Mass (m/e): 262 (M+).

(2) A mixture of methyl 1-(3-pyridylmethyl)-2,4-dioxopiperidine-3-carboxylate (8.50 g), acetonitrile (100 ml) and water (1.4 ml) is refluxed for one hour. The mixture is distilled to remove the solvent to give 1-(3-pyridylmethyl)-2,4-dioxopiperidine (6.66 g, quantitative) as crystals, m.p. 55°–60° C.

IR$\nu_{max}^{chloroform}$ (cm$^{-1}$): 1730, 1660.

NMR (CDCl$_3$)δ: 4.71 (s, 2H).

Mass (m/e): 204 (M+).

(3) 1-(3-Pyridylmethyl)-2,4-dioxopiperidine (2.01 g) is treated in the same manner as described in Example 1-(3), whereby 1-(3-pyridylmethyl)-3-(1,3-dithiol-2-ylidene)-2,4-dioxopiperidine (1.50 g, 50.1%) is obtained as yellow plates.

The physico-chemical properties of this compound are identical with those of the sample obtained in Example 28.

EXAMPLE 30

(1) Aniline (93 g) is dissolved in ethanol (500 ml), and thereto is added dropwise ethyl acrylate (100 g) under ice-cooling. The mixture is stirred at 50° C. for 3 hours and then refluxed for 8 hours. The mixture is distilled to remove the solvent. The residue is distilled under reduced pressure to give N-phenyl-β-alnine ethyl ester (26.6 g), b.p. 119°–120° C./2 mmHg.

IR$\nu_{max}^{liquid}$ (cm$^{-1}$): 1725.

(2) N-Phenyl-β-alanine ethyl ester (24,25 g) is dissolved in benzene (60 ml), and thereto is added dropwise diketene (12 ml) at 70° C. The mixture is refluxed overnight. The mixture is distilled to remove the solvent to give crude N-phenyl-N-methoxycarbonylmethylcarbonyl-β-alanine ethyl ester (37.23 g). Said crude compound is dissolved in methanol (70 ml), and the mixture is added dropwise to a solution of sodium methoxide (prepared from 3.90 g of sodium) in methanol (70 ml) at 50° C. The mixture is stirred at 50° C. for 2 hours, and distilled to remove the solvent. The residue is dissolved in water, and the aqueous solution is extracted with ethyl acetate. The aqueous layer is neutralized with 10% HCl, and extracted with ethyl acetate. The extract is washed with a saturated sodium chloride solution, dried and then distilled to remove the solvent. The residue is purified by silica gel column chromatography (solvent, ethyl acetate:n-hexane=1:2) to give 1-phenyl-3-acetyl-2,4-dioxopiperidine (23.87 g, 81.6%) as oil.

IR$\nu_{max}^{liquid}$ (cm$^{-1}$): 1665.

NMR (CDCl$_3$)δ: 2.58 (s, 3H).

Mass (m/e): 231 (M+).

(3) 1-Phenyl-3-acetyl-2,4-dioxopiperidine (2.0 g) is dissolved in ethanol (60 ml), and thereto is added 10% HCl (30 ml). The mixture is refluxed for 7 hours. The mixture is distilled to remove the solvent, and the residue is dissolved in ethyl acetate. The solution is washed with a saturated sodium chloride solution, dried and then distilled to remove the solvent to give crude 1-phenyl-2,4-dioxopiperidine (1.12 g). Said crude compound (1.12 g) is dissolved in dimethoxyethane (30 ml), and the solution is added dropwise to a suspension of sodium hydride (60% dispersion in oil, 524 mg) in dimethoxyethane (30 ml). Said addition is carried out under ice-cooling. The mixture is stirred at the same temperature for 40 minutes. 2-Methylthio-1,30dithiolium iodide (1.64 g) is added to the mixture, and the mixture is stirred at room temperature for 3 hours. The mixture is poured into water, and extracted with ethyl acetate. The extract is washed with water, dried and then distilled to remove the solvent. The residue is purified by silica gel column chromatography (solvent, ethyl acetate:n-hexane=1:1), and then recrystallized from a mixture of ethyl acetate and n-hexane to give 1-phenyl-3-(1,3-dithiol-2-ylidene)-2,4-dioxopiperidine (354 mg) as yellow needles, m.p. 150.5°–152° C.

IR$\nu_{max}^{KBr}$ (cm$^{-1}$): 1630, 1600.
NMR (CDCl$_3$)δ: 7.3–7.6 (m, 7H), 2.91 (t, J=6.5 Hz, 2H), 3.92 (t, J=6.5 Hz, 2H).
Mass (m/e): 289 (M+).

EXAMPLE 31

A mixture of ethyl 2-(1,3-dithiol-2-ylidene)-2-(N-benzylcarbamoyl)acetate (1.0 g) and dimethylformamide (25 ml) is added dropwise to a suspension of sodium hydride (63% dispersion in oil, 144 mg) in dimethylformamide (10 ml). Said addition is carried out under ice-cooling. The mixture is stirred at the same temperature for 30 minutes. A solution of diethyl maleate (0.6 ml) in dimethylformamide (10 ml) is added dropwise thereto. The mixture is stirred at room temperature overnight. The mixture is poured into water, and extracted with ethyl acetate. The extract is washed with a saturated sodium chloride solution, dried and then distilled to remove the solvent. The mixture is purified by silica gel column chromatography (solvent, n-hexane:ethyl acetate=1:2) to give 1-benzyl-5-(1,3-dithiol-2-ylidene)-4,6-dioxopiperidine-2,3-dicarboxylic acid diethyl ester (196 mg) as yellow oil.

IR$\nu_{max}^{chloroform}$ (cm$^{-1}$): 1735, 1630, 1600.
NMR (CDCl$_3$)δ: 1.17 (t, J=7 Hz, 3H), 1.07 (t, J=7 Hz, 3H), 5.41 (d, J=15 Hz, 1H), 4.17 (d, J=15 Hz, 1H), 7.40 (d, J=6.5 Hz, 1H), 7.36 (d, J=6.5 Hz, 1H).
Mass (m/e): 447 (M+).

EXAMPLE 32

(1) A mixture of p-nitrobenzaldehyde (1.51 g), β-alanine methyl ester hydrochloride (1.40 g), triethylamine (1.6 ml) and methanol (20 ml) is stirred at room temperature for 25 minutes. The mixture is ice-cooled, and sodium borohydride (807 mg) is added thereto. The mixture is stirred at the same temperature for 10 minutes. The mixture is acidified with 10% HCl, and extracted with ethyl acetate. The aqueous layer is neutralized with 10% NaOH, and extracted with ethyl acetate. The extract is washed with a saturated sodium chloride solution, dried and then distilled to remove the solvent. The residue is dissolved in ether, and a HCl-ether solution is added thereto. The precipitates are collected and recrystallized from methanol to give N-(p-nitrobenzyl)-β-alanine methyl ester hydrochloride (1.95 g, 71.1%) as pale yellow plates, m.p. 219.5°–220° C. (decomp.).

IR$\nu_{max}^{nujol}$ (cm$^{-1}$): 1730.
NMR (DMSO-d$_6$)δ: 4.33 (s, 2H).

(2) N-(p-Nitrobenzyl)-β-alanine methyl ester hydrochloride (32.66 g) and triethylamine (38 ml) are dissolved in methylene chloride (200 ml), and a solution of ethoxycarbonylacetyl chloride (20.0 g) in methylene chloride (100 ml) is added dropwise to the mixture under ice-cooling. The mixture is stirred at the same temperature for one hour, and the mixture is filtered to remove precipitates (triethylamine hydrochloride). The filtrate is washed with 2% HCl, water, 2% NaOH and water, dried and then distilled to remove the solvent to give ethyl[N-(p-nitrobenzyl)-N-(methoxycarbonylethyl)carbamoyl]acetate (40.4 g, 96.4%) as yellow oil.

IR$\nu_{max}^{liquid}$ (cm$^{-1}$): 1735, 1650.
NMR (CDCl$_3$)δ: 4.72 (s, 2H).
Mass (m/e): 352 (M+).

(3) Sodium (690 mg) is dissolved in ethanol (25 ml), and thereto is added dropwise a solution of ethyl[N-(p-nitrobenzyl)-N-(methoxycarbonylethyl)carbamoyl]acetate (10.0 g) in benzene (160 ml) at room temperature. The mixture was stirred at the same temperature for 1.5 hours. The mixture is poured into water. The aqueous layer is separated, neutralized with 10% HCl and extracted with ethyl acetate. The extract is washed with a saturated sodium chloride solution, dried and then distilled to remove the solvent to give ethyl 1-(p-nitrobenzyl)-2,4-dioxopiperidine-3-carboxylate (8.03 g, 88.4%) as yellow oil.

IR$\nu_{max}^{liquid}$ (cm$^{-1}$): 1720, 1645.
NMR (CDCl$_3$) δ: 4.70 (s, 2H).
Mass (m/e): 320 (M+).

(4) Ethyl 1-(p-nitrobenzyl)-2,4-dioxopiperidine-3-carboxylate (780 mg) is treated in the same manner as described in Example 29-(2), whereby 1-(p-nitrobenzyl)-2,4-dioxopiperidine (608 mg, quantitative) is obtained as a crude product.

Mass (m/e): 248 (M+).

Thus-obtained product (562 mg) is treated in the same manner as described in Example 1-(3), whereby 1-(p-nitrobenzyl)-3-(1,3-dithiol-2-ylidene)-2,4-dioxopiperidine (446 mg, 56.9%) is obtained as yellow needles.

m.p. 192°–193° C. (recrystallized from ethyl acetate).
IR$\nu_{max}^{nujol}$ (cm$^{-1}$): 1620, 1580.
NMR (CDCl$_3$) δ: 4.85 (s, 2H), 7.34 (s, 2H).
Mass (m/e): 348 (M+).

EXAMPLE 33

1-(p-Nitrobenzyl)-3-(1,3-dithiol-2-ylidene)-2,4-dioxopiperidine (100 mg) is dissolved in ethanol (20 ml), and thereto is added 10% Pd/C (100 mg). The mixture is subjected to catalytic reduction under atmospheric pressure. The mixture is filtered to remove the catalyst. The filtrate is distilled to remove the solvent to give 1-(p-aminobenzyl)-3-(1,3-dithiol-2-ylidene)-2,4-dioxopiperidine (92 mg, quantitative) as crystals.

m.p. 156.5°–158.5° C. (recrystallized from ethanol).
IR$\nu_{max}^{nujol}$ (cm$^{-1}$): 3440, 3355, 1625, 1585.
NMR (CDCl$_3$) δ: 4.64 (s, 2H), 7.26 (d, J=6 Hz, 1H), 7.32 (d, J=6 Hz, 1H).
Mass (m/e): 318 (M+).
Hydrochloride
Pale yellow needles.
m.p. 212° C. (decomp., recrystallized from methanolether).

EXAMPLE 34

(1) Ethyl[N-(p-nitrobenzyl)-N-(methoxycarbonylethyl)carbamoyl]acetate (1.01 g) obtained in Example 32-(2), ethanol (10 ml) and 10% Pd/C (150 mg) are treated in the same manner as described in Example 33, whereby ethyl[N-(p-aminobenzyl)-N-(methoxycarbonylethyl)carbamoyl]acetate (810 mg, 87.5%) is obtained as pale yellow oil.

IR$\nu_{max}^{chloroform}$ (cm$^{-1}$): 1735, 1640.
Mass (m/e): 322 (M+).

(2) A solution of benzyloxycarbonyl chloride (539 mg) in benzene (1.5 ml) is added dropwise to a mixture of ethyl[N-(p-aminobenzyl)-N-(methoxycarbonylethyl)carbamoyl]acetate (810 mg), potassium carbonate (595 mg), benzene (10 ml) and water (10 ml) at a temperature of 8° C. under stirring. The mixture is stirred at the same temperature for 30 minutes. The mixture is extracted with ethyl acetate, and the extract is washed with water, dried and then distilled to remove the solvent. The residue is purified by silica gel column chromatography (solvent, ethyl acetate:benzene=3:7) to give ethyl[N-(p-(N-benzyloxycarbonylamino)benzyl)-N-(methoxycarbonylethyl)carbamoyl]acetate (1.08 g, 94.2%) as colorless oil.

IR$\nu_{max}^{liquid}$ (cm$^{-1}$): 1720, 1630.
NMR (CDCl$_3$) δ: 5.17 (s, 2H).
Mass (m/e): 456 (M+).

(3) A solution of ethyl[N-(p-(N-benzyloxycarbonylamino)benzyl)-N-(methoxycarbonylethyl)carbamoyl]acetate (967 mg) in benzene (15 ml) is added dropwise to a solution of sodium ethoxide (prepared from sodium (60 mg) and ethanol (2 ml)) at room temperature. The mixture is stirred at the same temperature for 30 minutes. The mixture is poured into water. The aqueous solution is neutralized with 10% HCl, and extracted with ethyl acetate. The extract is washed with a saturated sodium chloride solution, dried and then distilled to remove the solvent to give ethyl 1-(p-(N-benzyloxycarbonylamino)-benzyl)-2,4-dioxopiperidine-3-carboxylate (841 mg, 93.5%) as colorless oil.

IR$\nu_{max}^{nujol}$ (cm$^{-1}$): 1725, 1640, 1600.
NMR (CDCl$_3$) δ: 4.56 (s, 2H).
Mass (m/e): 424 (M+).

(4) Ethyl 1-(p-(N-benzyloxycarbonylamino)benzyl)-2,4-dioxopiperidine-3-carboxylate (823 mg) is treated in the same manner as described in Example 29-(2), whereby 1-(p-(N-benzyloxycarbonylamino)benzyl)-2,4-dioxopiperidine (693 mg) is obtained as a crude product.

Mass (m/e): 352.

Thus-obtained product (660 mg) is treated in the same manner as described in Example 1-(3), whereby 1-(p-(N-benzyloxycarbonylamino)benzyl)-3-(1,3-dithiol-2-ylidene)-2,4-dioxopiperidine (518 mg, 62.0%) is obtained as pale yellow plates.

m.p. 175°–176.5° C. (recrystallized from ethyl acetate).

IR$\nu_{max}^{nujol}$ (cm$^{-1}$): 1725, 1620, 1580.
NMR (CDCl$_3$) δ: 4.69 (s, 2H), 5.18 (s, 2H), 7.15–7.5 (m, 11H).
Mass (m/e): 452 (M+).

EXAMPLE 35

1-(p-(N-Benzylcarbonylamino)benzyl)-3-(1,3-dithiol-2-ylidene)-2,4-dioxopiperidine (100 mg) is dissolved in acetic acid (2 ml), and a 25% HBr-acetic acid solution (0.5 ml) is added thereto. The mixture is stirred at room temperature for 40 minutes, and then at 40°–50° C. for one hour. After cooling the mixture, ether is added to the mixture. The precipitated crystals are collected by filtration, and recrystallized from a mixture of methanol and ether to give 1-(p-aminobenzyl)-3-(1,3-dithiol-2-ylidene)-2,4-dioxopiperidine hydrobromide (70 mg, 79.3%) as pale yellow needles, m.p. 210°–214° C. (decomp.).

IR$\nu_{max}^{nujol}$ (cm$^{-1}$): 1620, 1580.
NMR (DMSO-d$_6$) δ: 4.68 (s, 2H), 7.68 (d, J=6 Hz, 1H), 7.74 (d, J=6 Hz, 1H).
Mass (m/e): 318 (M+).

What is claimed is:

1. A compound of the fomula:

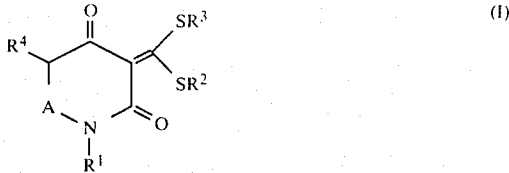

wherein
R$^1$ is hydrogen atom, an alkyl group of 1 to 10 carbon atoms, a lower alkenyl group, a phenyl group or a group of the formula: —B—Y;
Y is a pyridyl group, a pyrrolyl group, a phenyl group or a phenyl group having one or two substituents selected from the group consisting of a halogen atom, a lower alkyl, a lower alkoxy, nitro, amino and benzyloxycarbonylamino;
B is a straight or branched lower alkylene group;
R$^2$ and R$^3$ are both a lower alkyl group or are combined together to form a group of the formula: —CH$_2$CH$_2$— or —CH=CH—;
R$^4$ is hydrogen atom, a lower alkyl group or a (lower alkoxy)carbonyl group;
A is a group of the formula: —(CH$_2$)$_n$— or —CH(COOR$^5$)—;
n is an integer of 0, 1 or 2; and
R$^5$ is a lower alkyl group; or a pharmaceutically acceptable salt thereof.

2. A pharmaceutically acceptable salt of the compound of claim 1, wherein R$^1$ is a group of the formula: —B—Y wherein Y is a pyridyl group or an amino-phenyl.

3. The compound or pharmaceutically acceptable salt thereof of claim 1, wherein A is a group of the formula: —(CH$_2$)$_n$— or —CH(COOR$^5$)— and n is an integer of 1.

4. A pharmaceutically acceptable salt of the compound of claim 3, wherein R$^1$ is a group of the formula: —B—Y and Y is a pyridyl group or an amino-phenyl.

5. The compound or pharmaceutically acceptable salt thereof of claim 3, wherein R$^1$ is an alkyl group of 1 to 10 carbon atoms, a lower alkenyl group, a phenyl group or a group of the formula: —B—Y; and
R$^2$ and R$^3$ are combined together to form a group of the formula: —CH$_2$CH$_2$— or —CH=CH—.

6. A pharmaceutically acceptable salt of the compound of claim 5, wherein R$^1$ is a group of the formula: —B—Y and Y is a pyridyl group or an amino-phenyl.

7. The compound of claim 5, wherein R$^1$ is an alkyl group of 1 to 10 carbon atoms or a group of the formula: —B—Y;
Y is a phenyl group or a phenyl group having a substituent selected from a group consisting of a halogen atom or a lower alkoxy; and
B is a straight lower alkylene group.

8. The compound of pharmaceutically acceptable salt thereof of claim 1, wherein R$^1$ is hydrogen atom, methyl, ethyl, n-butyl, n-hexyl, n-octyl, n-decyl, allyl, phenyl, 3-pyridylmethyl, benzyl, phenethyl, 4-chlorobenzyl, 3,4-dichlorobenzyl, 4-methylbenzyl, 4-methoxybenzyl, 3,4-dimethoxybenzyl, 4-nitrobenzyl, 4-aminobenzyl or 4-(N-benzyloxycarbonylamino)benzyl;
R$^2$ and R$^3$ are both methyl or are combined together to form a group of the formula: —CH$_2$CH$_2$— or —CH=CH—;

$R^4$ is hydrogen atom, methyl, ethyl or ethoxycarbonyl;

A is a group of the formula: —$(CH_2)_n$— or —CH($COOR^5$)—;

n is an integer of 0, 1 or 2; and $R^5$ is ethyl.

9. A pharmaceutically acceptable salt of the compound of claim 8, wherein $R^1$ is 3-pyridylmethyl or 4-aminobenzyl.

10. The compound or pharmaceutically acceptable salt thereof of claim 8, wherein $R^1$ is methyl, ethyl, n-butyl, n-hexyl, allyl, phenyl, 3-pyridylmethyl, benzyl, phenethyl, 4-chlorobenzyl, 4-methylbenzyl, 4-methoxybenzyl or 3,4-dimethoxybenzyl;

$R^2$ and $R^3$ are combined together to form a group of the formula: —$CH_2CH_2$ or —CH=CH—;

A is a group of the formula: —$(CH_2)_n$— or —CH($COOR^5$)—;

n is an integer of 1.

11. A pharmaceutically acceptable salt of the compound of claim 10, wherein $R^1$ is 3-pyridylmethyl.

12. The compound of claim 10, wherein $R^1$ is methyl, ethyl, benzyl, 4-chlorobenzyl or 4-methoxybenzyl.

13. The compound of claim 12, which is 1-benzyl-3-(1,3-dithiol-2-ylidene)-2,4-dioxopiperidine.

14. The compound of claim 1, wherein the lower alkyl groups, the lower alkoxy groups and the lower alkylene groups each have 1 to 4 carbon atoms, respectively.

15. The compound of claim 1, wherein the lower alkenyl group has 2 to 4 carbon atoms.

16. A pharmaceutical composition for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of the compound as claimed in claim 1 in admixture with a pharmaceutically acceptable carrier or diluent.

17. A pharmaceutical composition for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis, which comprises as an essential active ingredient a therapeutically or prophylatically effective amount of the salt as claimed in claim 2 in admixture with a pharmaceutically acceptable carrier or diluent.

18. A pharmaceutical composition for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis, which comprises as an essential active ingredient a therapeutically or prophylatically effective amount of the compound as claimed in claim 3 in admixture with a pharmaceutically acceptable carrier or diluent.

19. A method for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis which comprises orally or parenterally administering 0.01 to 250 mg/kg/day of the compound of claim 1 to a subject.

20. The method of claim 19, wherein 0.1 to 50 mg/kg/day of said compound is administered orally or parenterally.

* * * * *